(12) United States Patent
Palmer et al.

(10) Patent No.: US 6,458,139 B1
(45) Date of Patent: Oct. 1, 2002

(54) FILTER/EMBOLI EXTRACTOR FOR USE IN VARIABLE SIZED BLOOD VESSELS

(75) Inventors: Olin J. Palmer, Mountain View; David Hancock, deceased, late of San Francisco, by Katherine Hancock, executor; Larry Voss, San Jose; Christopher G. M. Ken, San Mateo, all of CA (US)

(73) Assignee: Endovascular Technologies, Inc., Menlo Park, CA (US)

( * ) Notice: Subject to any disclaimer, the term of this patent is extended or adjusted under 35 U.S.C. 154(b) by 33 days.

(21) Appl. No.: 09/599,146

(22) Filed: Jun. 21, 2000

Related U.S. Application Data

(60) Provisional application No. 60/140,131, filed on Jun. 21, 1999.

(51) Int. Cl.⁷ .................................................. A61B 17/24
(52) U.S. Cl. ........................................ 606/113; 606/200
(58) Field of Search ............................... 606/159, 113, 606/114, 127, 200

(56) References Cited

U.S. PATENT DOCUMENTS

| | | |
|---|---|---|
| 2,943,626 A | 7/1960 | Dormia |
| 3,472,230 A | 10/1969 | Fogarty |
| 3,635,223 A | 1/1972 | Klieman |
| 3,868,956 A | 3/1975 | Alfidi |
| 3,978,863 A | 9/1976 | Fettel |
| 3,996,938 A | 12/1976 | Clark, III |
| 4,030,503 A | 6/1977 | Clark, III |
| 4,611,594 A | 9/1986 | Grayhack et al. |
| 4,612,931 A | 9/1986 | Dormia |
| 4,619,246 A | 10/1986 | Molgaard-Nielsen |
| 4,643,184 A | 2/1987 | Mobin-Uddin |
| 4,646,736 A | 3/1987 | Auth |
| 4,650,466 A | 3/1987 | Luther |
| 4,706,671 A | 11/1987 | Weinrib |
| 4,727,873 A | 3/1988 | Mobin-Uddin |
| 4,762,130 A | 8/1988 | Fogarty |
| 4,790,812 A | 12/1988 | Hawkins, Jr. |
| 4,832,055 A | 5/1989 | Palestrant |
| 4,865,017 A | 9/1989 | Shinozuka |
| 4,873,978 A | 10/1989 | Ginsburg |
| 4,885,003 A | 12/1989 | Hillstead |
| 4,890,611 A | 1/1990 | Monfort |
| 4,921,484 A | 5/1990 | Hillstead |
| 4,926,858 A | 5/1990 | Gifford, III |
| 4,969,891 A | 11/1990 | Gewertz |
| 4,997,435 A | 3/1991 | Demeter |
| 4,998,539 A | 3/1991 | Delsanti |
| 5,011,488 A | 4/1991 | Ginsburg |
| 5,034,001 A | 7/1991 | Garrison et al. |
| 5,041,093 A | 8/1991 | Chu |
| 5,047,040 A | 9/1991 | Simpson |
| 5,053,008 A | 10/1991 | Bajaj |
| 5,057,114 A | 10/1991 | Wittich et al. |
| 5,064,428 A | 11/1991 | Cope |
| 5,092,839 A | 3/1992 | Kipperman |

(List continued on next page.)

FOREIGN PATENT DOCUMENTS

| | | |
|---|---|---|
| EP | 0 418 677 A1 | 3/1991 |
| EP | 0 472 368 B1 | 6/1995 |
| JP | 10(1998)151136 | 6/1998 |
| WO | WO 94/24946 | 11/1994 |
| WO | WO 96/01591 | 1/1996 |

*Primary Examiner*—Kevin T. Truong
(74) *Attorney, Agent, or Firm*—Fulwider Patton Lee & Utecht, LLP

(57) ABSTRACT

An extraction device for the removal of clots and foreign bodies from vasculature. The extractor device is connected to an elongate mandrel and is located within a longitudinally extending lumen defined by a catheter. A clot or foreign material extracted from a vessel by moving the extraction device and catheter proximally until the clot or foreign material does not perfuse a critical organ.

10 Claims, 8 Drawing Sheets

U.S. PATENT DOCUMENTS

| | | |
|---|---|---|
| 5,100,423 A | 3/1992 | Fearnot |
| 5,102,415 A | 4/1992 | Guenther |
| 5,112,347 A | 5/1992 | Taheri |
| 5,133,733 A | 7/1992 | Rasmussen |
| 5,152,777 A | 10/1992 | Goldberg |
| 5,171,233 A | 12/1992 | Amplatz et al. |
| 5,180,368 A | 1/1993 | Garrison |
| 5,190,557 A | 3/1993 | Borodulin |
| 5,192,286 A | 3/1993 | Phan |
| 5,192,290 A | 3/1993 | Hilal |
| 5,221,261 A | 6/1993 | Termin et al. |
| 5,222,971 A | 6/1993 | Willard |
| 5,324,304 A | 6/1994 | Rasmussen |
| 5,329,942 A | 7/1994 | Gunther |
| 5,330,482 A | 7/1994 | Gibbs |
| 5,330,484 A | 7/1994 | Gunther et al. |
| 5,354,310 A | 10/1994 | Garnic et al. |
| 5,370,653 A | 12/1994 | Cragg |
| 5,411,509 A | 5/1995 | Hilal |
| 5,421,832 A | 6/1995 | Lefebvre |
| 5,449,372 A | 9/1995 | Schmaltz |
| 5,490,859 A | 2/1996 | Mische |
| 5,496,277 A | 3/1996 | Termin et al. |
| 5,496,330 A | 3/1996 | Bates |
| 5,501,694 A | 3/1996 | Ressemann |
| 5,509,923 A | 4/1996 | Middleman et al. |
| 5,522,825 A | 6/1996 | Kropf |
| 5,527,282 A | 6/1996 | Segal |
| 5,527,326 A | 6/1996 | Hermann et al. |
| 5,540,707 A | 7/1996 | Ressemann et al. |
| 5,549,626 A | 8/1996 | Miller |
| 5,607,466 A | 3/1997 | Imbert |
| 5,626,602 A | 5/1997 | Gianotti et al. |
| 5,649,906 A | 7/1997 | Gory et al. |
| 5,669,933 A | 9/1997 | Simon et al. |
| 5,688,234 A | 11/1997 | Frisbie |
| 5,695,469 A | 12/1997 | Segal |
| 5,695,507 A | 12/1997 | Auth et al. |
| 5,695,518 A | 12/1997 | Laerum |
| 5,695,519 A | 12/1997 | Summers et al. |
| 5,702,413 A | 12/1997 | Lafontaine |
| 5,713,853 A | 2/1998 | Clark et al. |
| 5,720,754 A | 2/1998 | Middleman et al. |
| 5,720,764 A | 2/1998 | Naderlinger |
| 5,725,571 A | 3/1998 | Imbert |
| 5,746,767 A | 5/1998 | Smith |
| 5,749,883 A | 5/1998 | Halpern |
| 5,755,790 A | 5/1998 | Chevillon et al. |
| 5,766,191 A | 6/1998 | Trerotola |
| 5,769,816 A | 6/1998 | Barbut et al. |
| 5,769,871 A | 6/1998 | Mers Kelley et al. |
| 5,772,674 A | 6/1998 | Nakhjavan |
| 5,792,145 A | 8/1998 | Bates et al. |
| 5,792,156 A | 8/1998 | Perouse |
| 5,792,157 A | 8/1998 | Mische |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,304 A | 10/1998 | Hart |
| 5,827,324 A | 10/1998 | Cassell |
| 5,836,868 A | 11/1998 | Ressemann |
| 5,846,251 A | 12/1998 | Hart |
| 5,848,964 A | 12/1998 | Samuels |
| 5,868,708 A | 2/1999 | Hart |
| 5,868,754 A | 2/1999 | Levine |
| 5,876,367 A | 3/1999 | Kaganov et al. |
| 5,882,329 A | 3/1999 | Patterson et al. |
| 5,893,869 A | 4/1999 | Barnhart et al. |
| 5,895,398 A | 4/1999 | Wensel et al. |
| 5,895,400 A | 4/1999 | Abela |
| 5,895,410 A | 4/1999 | Forber et al. |
| 5,897,567 A | 4/1999 | Ressemann et al. |
| 5,902,263 A | 5/1999 | Patterson et al. |
| 5,904,690 A | 5/1999 | Middleman et al. |
| 5,908,435 A | 6/1999 | Samuels |
| 5,910,154 A | 6/1999 | Tsugita et al. |
| 5,911,734 A | 6/1999 | Tsugita et al. |
| 5,928,261 A | 7/1999 | Ruiz |
| 5,935,139 A | 8/1999 | Bates |
| 6,053,932 A | 4/2000 | Daniel |
| 6,168,603 B1 | 1/2001 | Leslie et al. |
| 6,231,589 B1 * | 5/2001 | Wessman et al. ........... 606/200 |

* cited by examiner

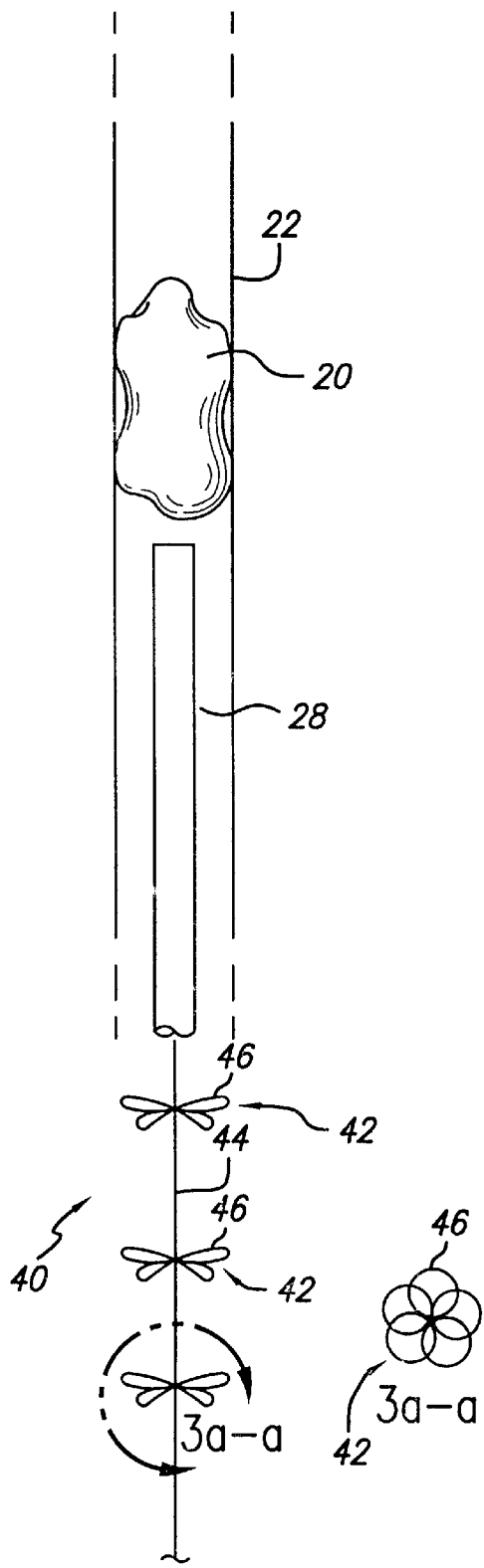
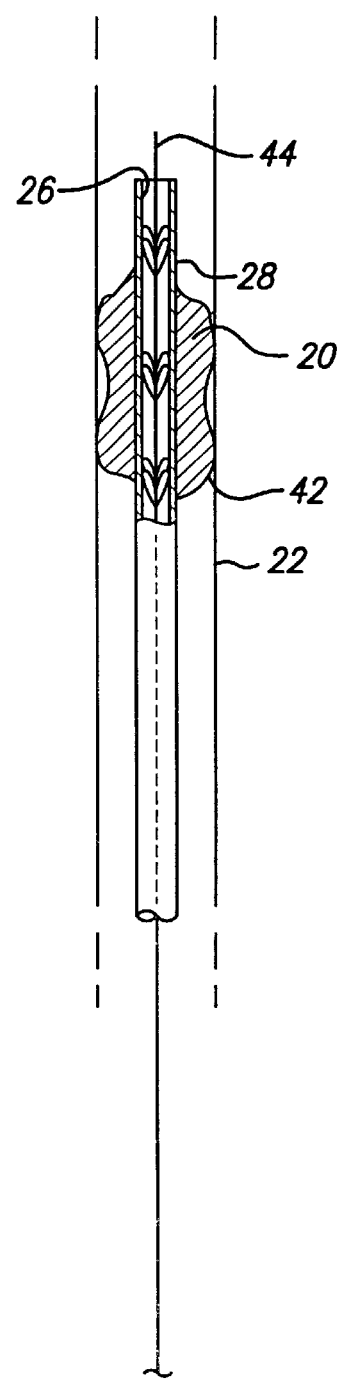

FIG. 3c
FIG. 3d
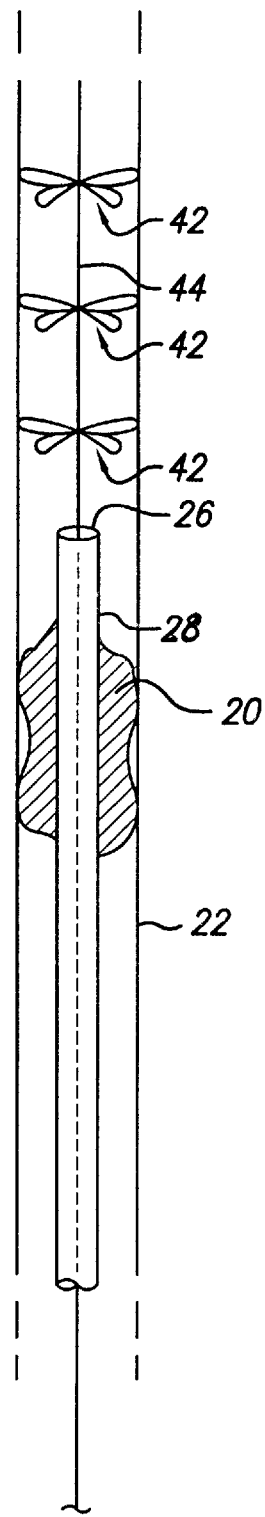
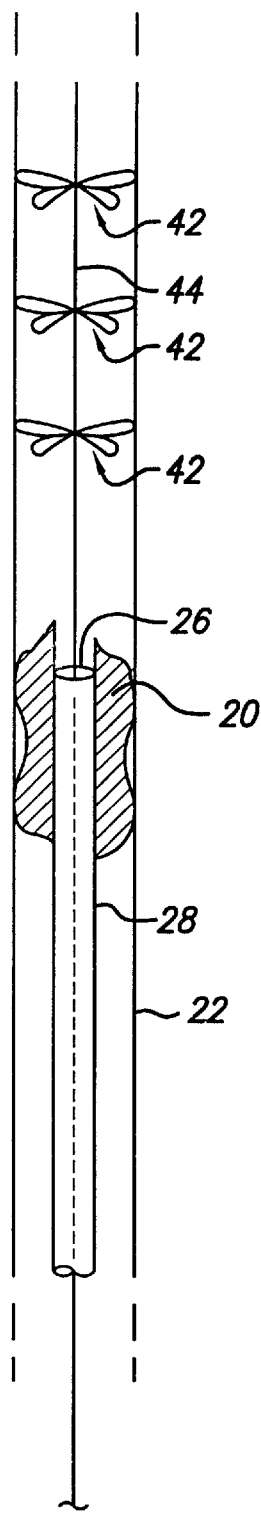

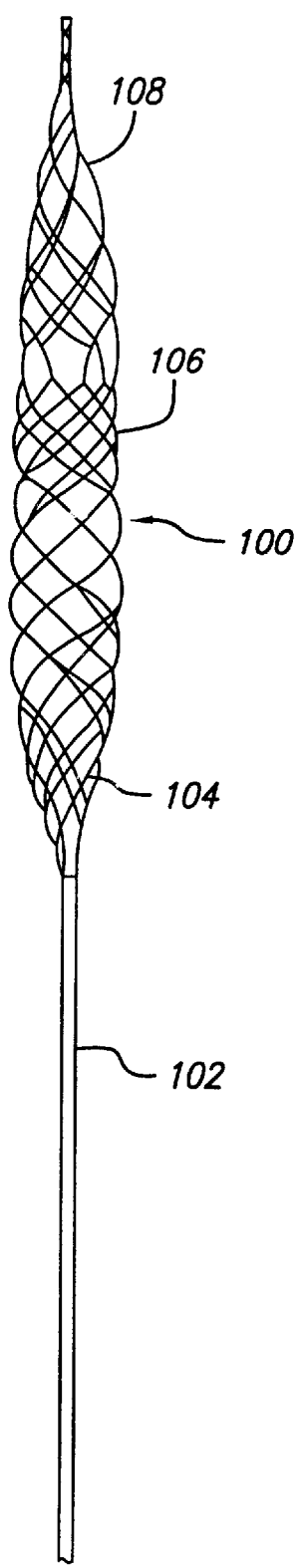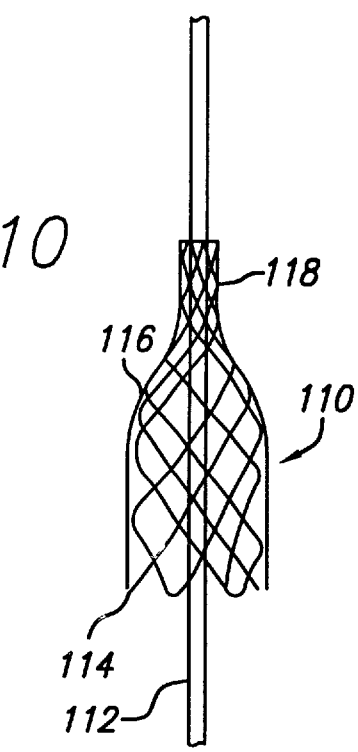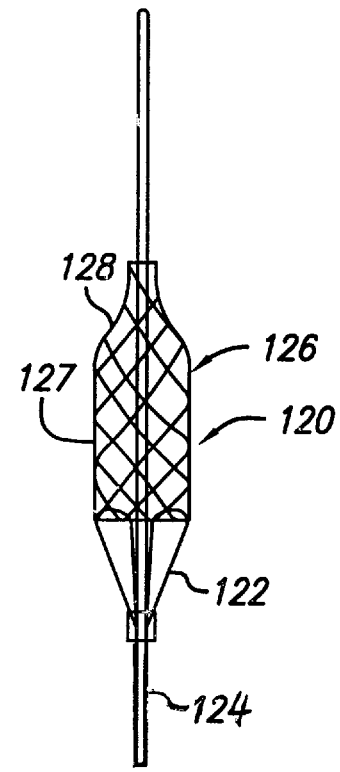

FILTER/EMBOLI EXTRACTOR FOR USE IN VARIABLE SIZED BLOOD VESSELS

RELATED APPLICATIONS

This is based upon the provisional application Serial No. 60/140,131 filed Jun. 21, 1999, entitled "FILTER/EMBOLI EXTRACTOR FOR USE IN VARIABLE SIZED BLOOD VESSELS."

BACKGROUND OF THE INVENTION

The present invention relates to medical devices that are useful in treating thromboembolic disorders and for removal of foreign bodies in the vascular system.

Thromboembolic disorders, such as stroke, pulmonary embolism, peripheral thrombosis, atherosclerosis, and the like, affect many people. These disorders are a major cause of morbidity and mortality in the United States.

Thromboembolic events are characterized by an occlusion of a blood vessel. The occlusion is caused by a clot which is viscoelastic (jelly like) and is comprised of platelets, fibrinogen and other clotting proteins.

When an artery is occluded by a clot, tissue ischemia (lack of oxygen and nutrients) develops. The ischemia will progress to tissue infarction (cell death) if the occlusion persists. Infarction does not develop or is greatly limited if the flow of blood is reestablished rapidly. Failure to reestablish blood-flow can lead to the loss of limb, angina pectoris, myocardial infarction, stroke or even death.

Occlusion of the venous circulation by thrombi leads to blood stasis which can cause numerous problems. The majority of pulmonary embolisms are caused by emboli that originate in the peripheral venous system. Reestablishing blood flow and removal of the thrombus is highly desirable.

There are many existing techniques employed to reestablish blood flow in an occluded vessel. One common surgical technique, an embolectomy, involves incising a blood vessel and introducing a balloon-tipped device (such as the Fogarty catheter) to the location of the occlusion. The balloon is then inflated at a point beyond the clot and used to translate the obstructing material back to the point of incision. The obstructing material is then removed by the surgeon. While such surgical techniques have been useful, exposing a patient to surgery may be traumatic and best avoided when possible. Additionally, the use of a Fogarty catheter maybe problematic due to the possible risk of damaging the interior lining of the vessel as the catheter is being withdrawn.

Percutaneous methods are also utilized for reestablishing blood flow. A common percutaneous technique is referred to as balloon angioplasty where a balloon-tipped catheter is introduced to a blood vessel, typically through an introducing catheter. The balloon-tipped catheter is then advanced to the point of the occlusion and inflated in order to dilate the stenosis. Balloon angioplasty is appropriate for treating vessel stenosis but is generally not effective for treating acute thromboembolisms.

Another percutaneous technique is to place a microcatheter near the clot and infuse streptokinase, urokinase or other thrombolytic agents to dissolve the clot. Unfortunately, thrombolysis typically takes hours to days to be successful. Additionally, thrombolytic agents can cause hemorrhage and in many patients the agents cannot be used at all.

Another problematic area is the removal of foreign bodies. Foreign bodies introduced into the circulation can be fragments of catheters, pace-maker electrodes, guide wires, and erroneously placed embolic material such as thrombogenic coils. There exists retrieval devices for the removal of foreign bodies, certain of such devices form a loop that can ensnare the foreign material by decreasing the size of the diameter of the loop around the foreign body. The use of such removal devices can be difficult and sometimes unsuccessful.

Various thrombectomy and foreign matter removal devices have been disclosed in the art. However, such devices have been found to have structures which are either highly complex or lacking in sufficient retaining structure. Disadvantages associated with the devices having highly complex structure include difficulty in manufacturability as well as use in conjunction with microcatheter. Other less complex devices tend to pull through clots due to in part to the lack of experience in using the same or are otherwise inadequate in capturing clots or foreign bodies.

Moreover, systems heretofore disclosed in the art are generally limited by size compatibility and the increase in vessel size as the emboli is drawn out in the distal vascular occlusion location to a more proximal location near the heart. If the embolectomy device is too large for the vessel it will not deploy correctly to capture the clot or foreign body and if too small in diameter, it cannot capture clots or foreign bodies across the entire cross section of the blood vessel. Additionally, if the embolectomy device is too small in retaining volume, as the device is retracted, the excess material being removed can spill out and be carried by flow back to occlude another distal vessel.

Thus, there exists a need for an extraction device that can be easily deployed into the circulatory system for the effective removal of clots and foreign bodies. There is also a need for a device which could be used as a temporary arterial or venous filter to capture and remove thromboemboli formed during endovascular procedures.

SUMMARY OF THE INVENTION

The present invention is directed to devices that are useful in removing clots and foreign bodies from vessels. Various embodiments and method of use are disclosed for the effective removal of clots or foreign bodies. It is contemplated that the present invention may be used in all vasculature including the neurovasculature.

In one aspect of the invention, an elongate generally linear wire is provided for the removal of certain types of undesirable matter found in a blood vessel. The elongate generally linear wire is placed within the undesirable matter and rotated to thereby catch the matter and wind it about the wire. Withdrawing the wire within a receiving tube or directly through the vessel operates to extract the undesirable matter from the patient's vasculature.

In another aspect of the invention, a staged filter/emboli extractor is provided to remove clots or foreign material from a vessel. In one embodiment, a plurality of spaced-apart radially extending structures are configured on an elongate wire or tubular mandrel proximal a distal end of the mandrel. The radially extending structures are characterized by increasing in size from the most proximal structure to the most distal structure. In a presently preferred embodiment, each of the radially extending structures are in the form of a plurality of loops or petals arranged in an annular radial array about the circumference of the mandrel. In an alternative embodiment, each of the plurality of loops or petals originate from a common side of the mandrel and can be concentrically arranged.

In yet a further aspect of the invention, a knitted or mesh structure is provided for the removal of clots or foreign material from a blood vessel. The knitted or mesh structure is configured near the distal end portion of an elongate wire or tubular mandrel. In one presently contemplated embodiment, the knitted or mesh structure is affixed in a conventional manner to the distal end of the mandrel. In another presently contemplated embodiment, the knitted or mesh structure surrounds a distal portion of the mandrel and may additionally embody structure enabling one end of the knitted or meshed structure to be translated longitudinally with respect to its other end which is held fixed. The knitted or mesh structures disclosed are further characterized by having open or closed ends or a basket-like configuration.

The invention also includes an elongate tubular delivery catheter with at least one lumen for receiving an extractor device and for retaining the distal portion thereof in a reduced profile. The delivery catheter may be used in conjunction with an elongate insertion catheter that is configured to be introduced into a large vessel and advanced within a patient's vasculature.

Generally, the clot is extracted from a vessel by capturing the same and withdrawing the clot or foreign material proximally until it can be removed or released into a different vessel that does not perfuse a critical organ. The structure disclosed can also be used as a temporary arterial or venous filter to capture and remove thromboemboli formed during endovascular procedures. By removing the device from the body, the clot or foreign material is also removed.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 3a is a schematic illustration depicting an occluded vessel with a catheter and a second embodiment of extraction device of the present invention;

FIG. 3b is a schematic illustration depicting the catheter of FIG. 3a shown in partial cross-section and being inserted through an occlusion;

FIG. 3c is a schematic illustration depicting the extraction device of 3a advanced longitudinally with respect to the catheter;

FIG. 3d is a schematic illustration depicting withdrawing the catheter and extraction device to ensnare a clot within an occluded vessel;

FIG. 9 depicts a sixth embodiment of the extraction device of the present invention;

FIG. 10 is a schematic illustration depicting a seventh embodiment of the extraction device of the present invention;

FIG. 11 is a schematic illustration depicting an eighth embodiment of the extraction device of the present invention;

DETAILED DESCRIPTION OF THE PREFERRED EMBODIMENTS

The present invention is useful for the removal of clots or foreign material from vasculature. The present invention is intended to be used in various sized vessels and in vessels having varying degrees of tortuosity. Of particular significance is the contemplated use of the preferred embodiment in the highly tortuous neurovasculature. Moreover, the disclosed extraction devices are characterized by having structure that is useful as filter devices.

Figure 1A:
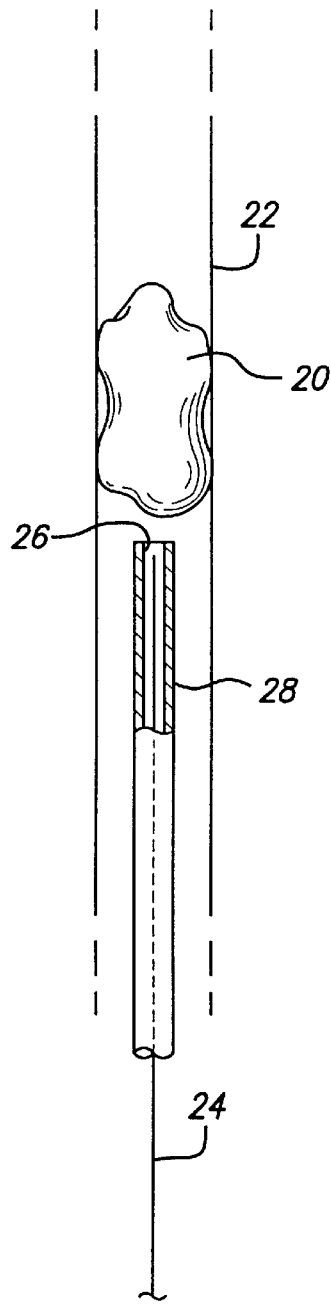
FIG. 1a is a schematic illustration depicting an occluded vessel with a catheter shown partially in cross-section and a first embodiment of an extraction device of the present invention.
Figure 1B:
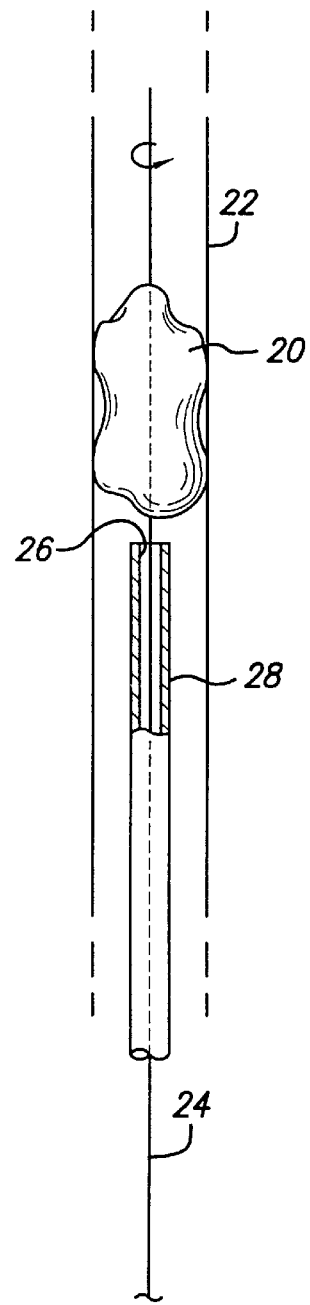
FIG. 1b is a schematic illustration depicting the extraction device of FIG. 1a inserted through an occlusion.
Figure 1C:
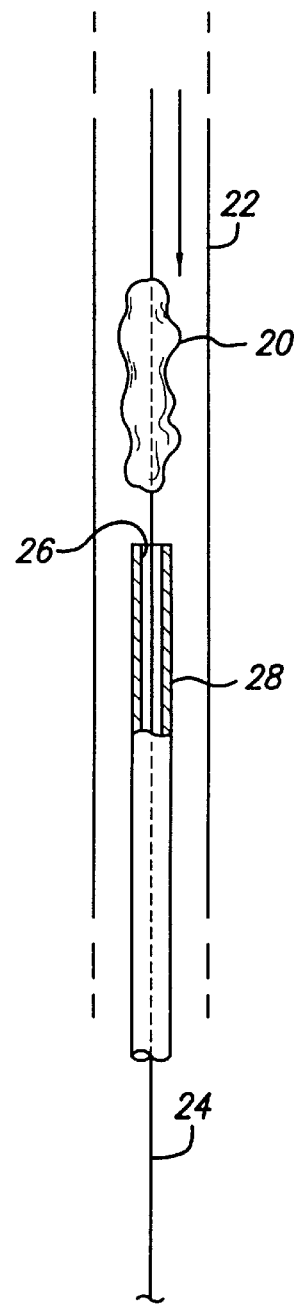
FIG. 1c is a schematic illustration depicting the extraction device of FIG. 1b withdrawing a clot from a vessel.

Referring to FIGS. 1a–c, there is shown a first embodiment of the present invention being used to extract a clot or foreign material 20 from a vessel 22. In the presently preferred first embodiment, an elongate wire 24 embodies an extraction device. The elongate wire 24 is configured longitudinally within a lumen 26 defined by an elongate tubular delivery catheter 28.

The elongate wire 24 may comprise a conventional guidewire or other wire structure having similar properties. One material of choice may be Nitinol. Its exterior may be scored or include other surface irregularities (not shown) for the purpose of enhancing engagement with certain types of clots or foreign bodies found in a patient's vasculature. Its outer diameter is such that it can easily slide within the lumen 26 of the catheter 28. Generally, the elongate wire 24 has a length greater than that of the catheter 28 so that its proximal end can be grasped by an operator and so that the elongate wire can be advanced and withdrawn independently of the catheter 28.

The delivery catheter 28 can be any commercially available catheter that is made out of any appropriate biologically compatible material. Typically, the catheter will have a single lumen 26 as constructed out of a flexible elastomeric material such as silicone, rubber, polyvinylchloride, polyeurothanes, polyesters, polytetrafluoroethylene and the like. The catheter has to be flexible enough and long enough to navigate through blood vessels to the occluded vessel where clots or other foreign bodies 20 are located. Typically the catheter will range in length from about 20 to about 175 centimeters.

The outer diameter of the catheter can also vary. Typically, the outer diameter will range from about 2 to about 10 F (1 F equals 0.013 inch). The inner diameter will range from about 1 to about 9 F.

In use, the elongate wire 24 and catheter 28 are inserted into a patient's vasculature using conventional techniques, using fluoroscopy or other conventional means. The elongate wire 24 and catheter 28 are advanced within a patient's vasculature 22 to the location proximal to the clot or foreign body 20 to be extracted. The elongate wire 24 is then advanced independently of the delivery catheter 28 and across the clot or foreign material 20. Next, the elongate wire 24 is rotated to thereby catch the clot or foreign material 20 and wind it about the elongate wire 24. Thereafter, the elongate wire 24 with the clot or foreign material adhered thereto is withdrawn within the delivery catheter 28 and both the elongate wire and-delivery catheter are removed from the patient's vasculature. Alternatively, the elongate wire 24 is directly removed from the patient's vasculature without first withdrawing it within the delivery catheter 28.

Figure 2A:
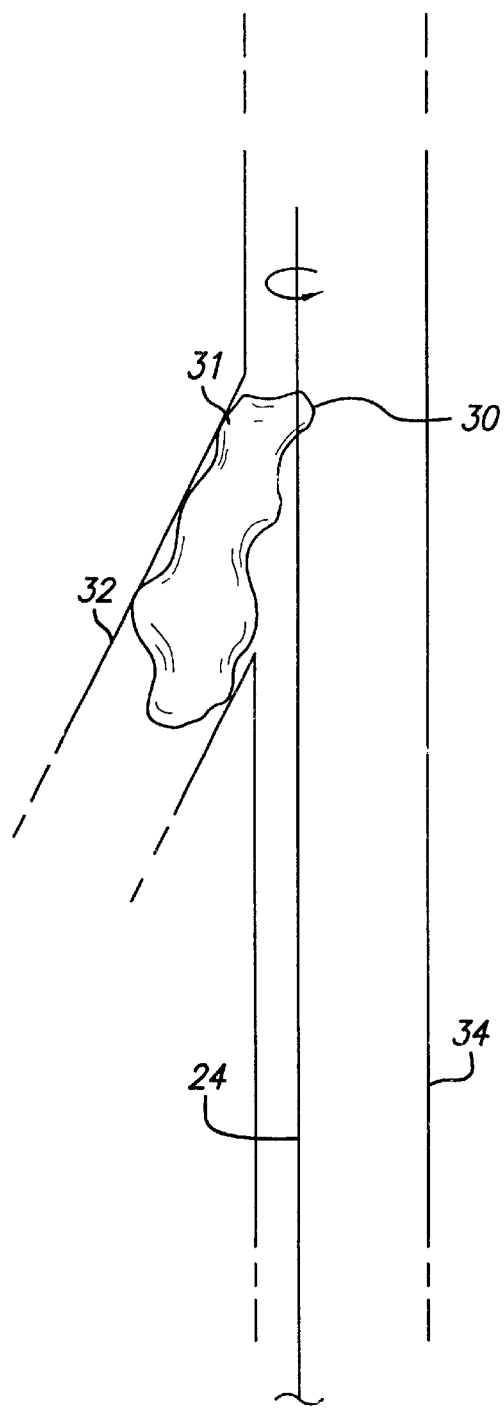
FIG. 2a is a schematic illustration depicting the extraction device of FIG. 1a encountering a clot in another area of vasculature.
Figure 2B:
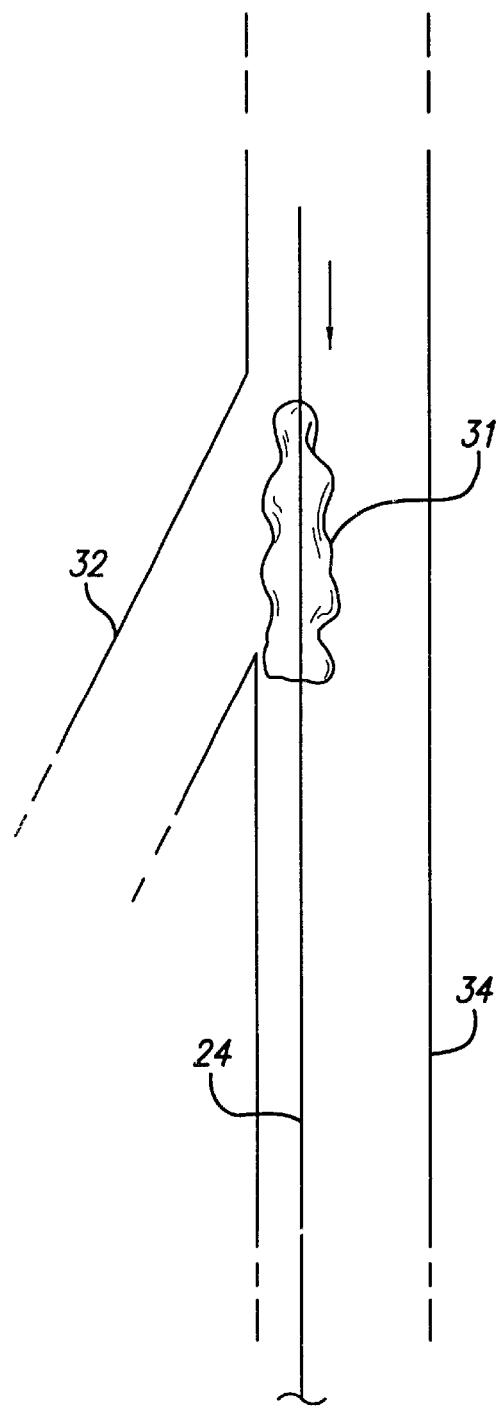
FIG. 2b is a schematic illustration depicting the extraction device of FIG. 2a withdrawing the clot from a vessel.

It has been observed that the elongate wire 24 is particularly useful in capturing fibrin clots. As shown in FIGS. 2a–b, the elongate wire 24 is useful even where there is just a small amount of fibrin tendril 30 of a clot 31 extending from a branch 32 into a parent lumen 34. In such a situation, the elongate wire 24 is placed adjacent the fibrin tendril 30 and is rotated to first catch the fibrin 30 and then wind the clot 31 about the elongate wire 24. The clot 31 can then be removed from the patient's vasculature by withdrawing the elongate wire 24.

A second preferred embodiment of the present invention is shown in FIGS. 3a–d. The second embodiment is a staged filter/emboli extractor 40 that includes a plurality of spaced-apart radially extending structures 42 configured on a mandrel 44. The radially extending structure 42 each embody a plurality of loops or petals 46 arranged in an angular radial array about the circumference of the mandrel 44. As shown in the break-out illustration included in FIG. 3a which depicts an end view of one radially extending structure 42, it is contemplated that each loop or petal 46 be configured to overlay at least a portion of the next adjacent petal in an over-under pattern such that each loop/petal 46 supports another loop/petal 46. It is also contemplated that each loop/petal can overlay/underlay two or more petals in a supporting fashion.

The number of petals or loops 46 of a radially extending structure 42 can range from 3–8 or more depending on the size of the petal or loop. The petal or loop itself can have a circular or generally oval configuration with its opening defining a space having a cross-section ranging from 0.050 inches or smaller to 2.125 inches and larger across. The wire used to form the loops 46 can be made of NiTi wire having a diameter ranging from 0.002–0.0055 inches or more.

In a preferred embodiment of the staged filter/emboli extractor 40, there are three spaced-apart radially extending structures formed on the mandrel 44. The petals/loops are configured to project from the mandrel 44 at a distally directed angle and are characterized by increasing in size or cross-sectional profile as one moves distally along the mandrel 44. However, it is to be recognized that as few as one and as many as eight or more radially extending structures can be configured on the mandrel 44. Moreover, depending on the application, the petals can project at a proximally directed angle and can either decrease in size or cross-sectional profile or vary as one moves distally along the mandrel 44.

The mandrel 44 has to be relatively stiff to support the staged filter/emboli extractor 40. In the preferred embodiment, the insertion mandrel is made out of stainless steel and is a solid wire from about 0.005 to about 0.038 inches in diameter. Other materials can be used such as hard plastic, Nitinol, and the like to make the insertion mandrel. The insertion mandrel is 10–20 centimeters longer than the catheter such that the operator of the device (typically a physician) can control the insertion mandrel 44 by gripping the proximal end which extends from the proximal end of the delivery catheter 28 with which it is used.

Figure 5A:
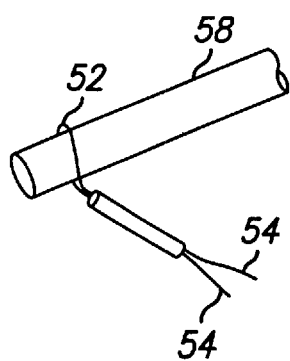
FIG. 5a is a schematic illustration depicting a first step in manufacturing the extraction device of FIG. 4.
Figure 5B:
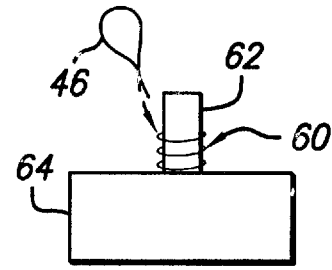
FIG. 5b is a schematic illustration depicting a second step of manufacturing the extraction device of FIG. 4.

With reference to FIGS. 5a–b, in order to manufacture the staged filter/emboli extractor 40, the wire defining the loops/petals is formed into a hoop 52 with its lead ends 54 inserted into an hypotube 56. The hoop portion 52 is placed over a petal mandrel 58 having an outer diameter of a particular dimension. Different sized petal mandrels are used for forming different sized hoops. The hypotube 56 is slid towards the petal mandrel 58 in order to form an appropriate sized hoop 52. Next, the hoop 52 is angled to a desirable degree with respect to the petal mandrel 58. Angles of 30° degrees or less and 80° degrees or more are contemplated. Thereafter, the wire 50 is heated for about thirty seconds with a heat gun to approximately 1100° degrees Fahrenheit for the purpose of annealing the wire 50 and setting the angle of the wire 50 with respect to the petal mandrel 58. The hypotube 56 is removed and the lead ends 54 of the wire are cut to a desired length. A desired number of loops/petals 46 are formed in this matter.

Next, a coil retainer 60 is slipped over a ceramic (non-solderable) rod 62 projecting from a support 64. The remaining lead ends 54 of the loops/petals 46 are then placed between the ceramic rod 62 and coil retainer 60. Thereafter, the remaining lead ends are soldered to the retainer 60. The soldered assembly is removed from the ceramic rod 62 and is ready to be affixed to the mandrel 44 in any conventional manner including soldering or using adhesives.

Multiple loops/petals 46 can alternatively be simultaneously manufactured using a similar procedure. Generally, manufacturing the loops/petals 46 can be accomplished by looping a single wire 50 about a combination of rods that form the loops/petals as well as an auxiliary rod from which the loops/petals originate. Thereafter, the multiple loops can be affixed directly to a mandrel 44 or first cut and then affixed thereto.

In operation (see FIGS. 3a–d), the staged filter/emboli extractor 40 is placed longitudinally within a lumen 26 defined by a catheter 28. It is to be recognized that when the staged filter/emboli extractor 40 is placed within the catheter 28, the individual loops/petals 46 are held in a compressed configuration. That is, the radially projecting structures 42 define a smaller cross-sectional profile when contained within the delivery catheter 28, the degree of reduction in profile being controlled by the inner diameter of the delivery catheter.

The extractor 40 and catheter 28 are then inserted into a patient's vasculature using conventional techniques. Using fluoroscopy or other conventional means, the extractor 40 and catheter 28 are advanced within a patient's vasculature 22 to a location proximal to the clot or foreign body 20 to be extracted. The delivery catheter 28 with extractor 40 contained therein is then advanced so that the delivery catheter 28 traverses the clot or foreign body 20 to be extracted. The staged filter/emboli retractor 40 is then advanced independently of the delivery catheter 28 so that the radially projecting structures 42 are positioned distally with respect to the clot or foreign body 20.

When the extractor 40 is so positioned, the radially projecting structures 42 are permitted to spring outwardly and assume an uncompressed or less compressed configuration, the angle of the loops/petals 46 with respect to the mandrel 44 being defined during the manufacturing process.

Subsequently, the staged filter/emboli extractor 40 is withdrawn into engagement with the clot or foreign material 20 for the purpose of capturing the same. While withdrawing the extractor 40 rotational movement may be applied for the purpose of enhancing the ability of the extractor 40 to capture the clot or foreign material 20. As the extractor and delivery catheter 28 are continued to be withdrawn proximally, the entirety of the clot or foreign material 20 is removed from the vessel. It is contemplated that the radially projecting structures 42 are relied upon to extract the clot or foreign body 20 without the interaction of the delivery catheter 28. Alternatively, it is also contemplated that the extractor be withdrawn within the delivery catheter once it has engaged and captured the clot or foreign material 20.

It is to be recognized that use of combined staged variable sized elements in a single device such as the staged filter/emboli extractor has a number of advantages. That is, when deployed in a distal anatomy, distal to an emboli for an example, the correct size radially extending structure 42 engages the emboli first. As the emboli is retracted to larger vessels, if the first radially extending structure 42 is too small in diameter or volume, any "spilled" material can be caught by a subsequent radially extending structure 42. Moreover, employing multiple radially extending structures 42 on the extractor 40 inherently has the advantage of engaging a clot or foreign material 20 a multiple of times, thereby assuring that any undesirable matter left behind after a first pass will be collected during subsequent passes.

Figure 4:
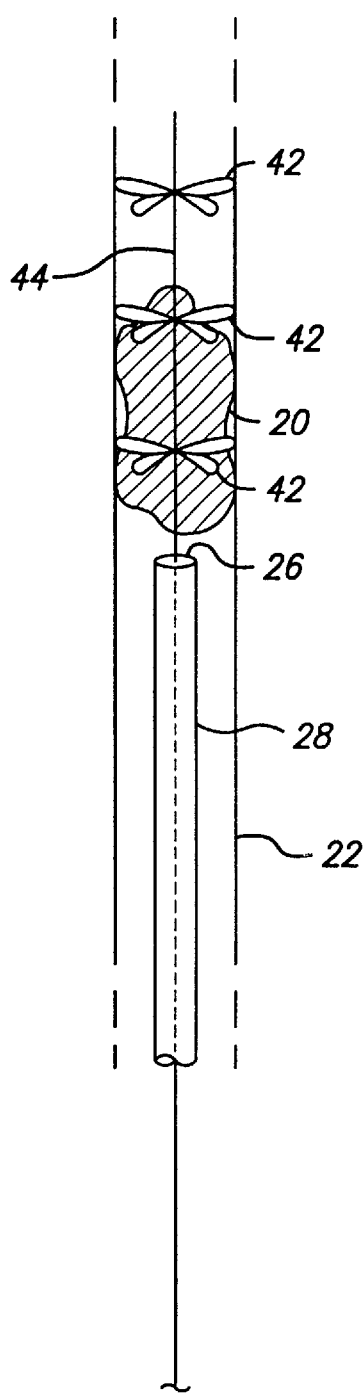
FIG. 4 is a schematic illustration depicting the second embodiment of the extraction device being deployed within an occlusion.

With reference to FIG. 4, it is also to be recognized that the staged filter/emboli extractor 40 can also be deployed directly within a clot or foreign material 20 for the purpose of removing the undesirable matter from the patient's vasculature. Thus, rather than deploying the extractor 40 distal to the undesirable matter and withdrawing the extractor 40 through the same, it is possible to also release the extractor 40 directly within the clot or foreign material 20. In practice, it may also be beneficial to deploy the extractor 40 so that the appropriate sized radially extending structure 42 first engages the clot or foreign matter 20. Once the extractor 40 has engaged and captured the undesirable matter, the extractor. 40 can be withdrawn proximally to remove such matter from the patient's vasculature.

Moreover, in certain situations it might be beneficial to employ a mandrel 44 which further includes a lumen (not shown) which extends substantially the length of the mandrel 44. Such a mandrel 44 could then be threaded over an appropriate sized guidewire in order to facilitate the advancement of the extractor 40 within a patient's vasculature.

Various other embodiments of extractors may be useful in removing undesirable material from blood vessels. Such other embodiments of extractors can be deployed distally with respect of the undesirable material and withdrawn or they can be directly deployed within such undesirable material and thereafter removed from the blood vessel. Moreover, other such embodiments of extractors may be used in conjunction with a delivery catheter 28 which operates to deliver the extractor to the repair site as well as releasably hold the extractor in a compressed configuration.

Figure 6:
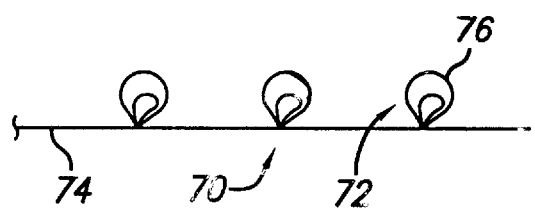
FIG. 6 depicts a third embodiment of the extraction device of the present invention.

As shown in FIG. 6, a third embodiment of an extractor 70 includes a plurality of spaced-apart asymmetric radially extending structures 72 originating from one side of the mandrel 74. By employing asymmetric radially extending structures, it maybe easier to manufacture the same. Additionally, such asymmetric radially extending structures may be compressed into a catheter lumen more easily and may more effectively handle corners or tortuous vasculature. As with the second embodiment of the present invention, a mandrel 74 can embody a solid or tubular structure. The asymmetric radially extending structures 72 can number from 1 to 8 or more and can each include a plurality of concentrically arranged loops or petals 76. The concentrically arranged loops or petals 76 of a particular asymmetric radially extending structure 72 can number from 2 to 5 or more depending on the application and innermost loop 78 can be a first cross-sectional size with subsequent loops concentrically arranged thereabout having ever increasing cross-sectional profiles.

In certain circumstances, it may be desirable to have the asymmetric radially extending structure 72 increasing in size as one moves distally along the mandrel 74. However, in other instances, the asymmetric radially extending structures 72 can decrease or otherwise vary in profile as one moves distally along the mandrel 74. Moreover, as with the second embodiment of the present invention, the asymmetric radially extending structures 72 are contemplated to angle distally with respect to the mandrel but can also be angled proximally. The same materials and similar manufacturing steps can be employed to produce the extractor 70. Furthermore, as stated, the extractor 70 can be used in conjunction with the delivery catheter 28 according to the method set forth above in connection with the prior embodiments of the present invention.

Referring to FIGS. 7–13, extractors employing knitted or mesh structures are shown. Such extractors can also be used in conjunction with a delivery catheter according to the methods set forth above in conjunction with the prior embodiments of the present invention. In particular, such extractors may be used in connection with a delivery catheter and can be rotated, and withdrawn to capture undesirable material.

Figure 7:
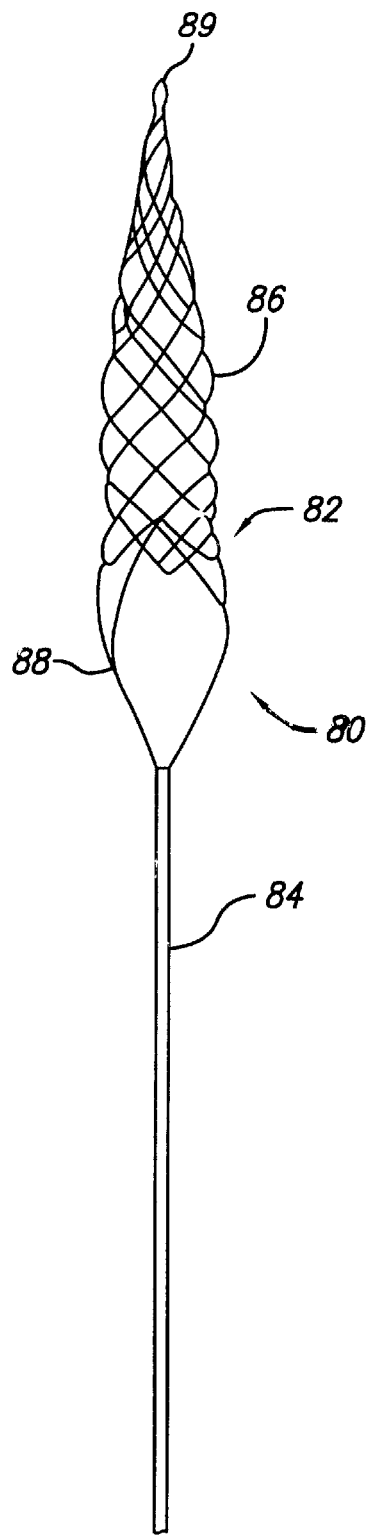
FIG. 7 depicts a fourth embodiment of the extraction device of the present invention.

As shown in FIG. 7, a fourth embodiment of the present invention embodies a knitted or mesh, hollow basket-like extractor 80 which includes a basket 82 attached to a mandrel 84. The mandrel 84 can be a solid or tubular structure. The basket 82 includes a mesh or knitted portion 86 connected by conventional means such as welding via a plurality of proximally extending arms 88 to the distal end of the mandrel 84. The knitted or mesh portion 86 may form a cone-like configuration with its most distal end 89 defining the apex of the cone. It is to be recognized, however, that other basket configurations may also be employed. The basket-like extractor 80 is characterized by providing structure which may be particularly useful in collecting matter in its hollow interior as blood flows therethrough.

Figure 8:
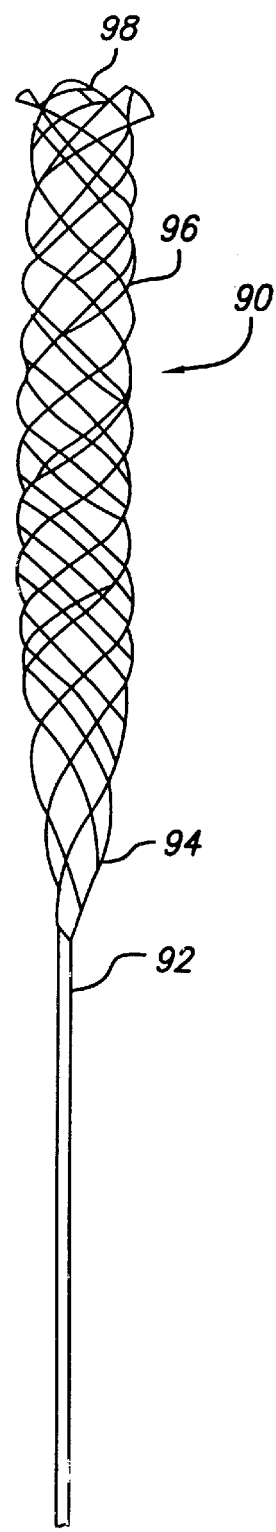
FIG. 8 depicts a fifth embodiment of the extraction device of the present invention.

As shown in FIG. 8, a fifth embodiment in the present invention includes a hollow knitted or mesh extractor 90 attached to a distal end of a solid or tubular mandrel 92. In this embodiment, the knitted or mesh portion has a cone-like proximal portion 94 that is welded or otherwise affixed to the distal end of the mandrel 92 as well as a generally cylindrical distal portion 96 which extends integrally from the proximal portion 94. The distal most end 98 of the knitted or mesh structure terminates at a generally right angle to a longitudinal axis of the knitted or mesh portion and further defines an opening to the hollow interior of the device. This device may provide a relatively larger cross-section for blood to flow through its distal end while the device continues to trap undesirable material in a blood vessel or compress the same against the vessel wall.

A sixth embodiment of the present invention is shown in FIG. 9. In this presently preferred embodiment, a knitted or mesh structure 100 is attached by conventional means such as welding to a distal end of a solid or tubular mandrel 102. The knitted or mesh structure 100 has a hollow interior and further includes a proximally directed cone-like portion 104 attached to the mandrel 102, a generally cylindrical mid-section 106 extending integrally from the proximal portion 104, and a distally directed cone-like portion 108 extending integrally from the generally cylindrical mid-section 106. Such a device may provide the advantage of improved deployability in that it might be more easily ejected from a delivery catheter and permitted to more fully expand.

A seventh embodiment of the present invention is shown in FIG. 10. In this contemplated embodiment, a knitted or mesh cup-like structure 110 is affixed to a solid or tubular mandrel 112 proximal to a distal end of the mandrel 112. The cup-like structure 110 includes a proximally directed, generally circular opening 114 which provides access to an interior of the hollow device. The cup-like structure 110 also includes a distal end portion 116 that narrows in a cone-like fashion, the distal most part 118 of which is attached to the mandrel 112. In certain circumstances, it may be desirable to employ a collar (not shown) to aid in so affixing the device to the mandrel 112.

As shown in FIG. 11, an eighth embodiment of the present invention embodies a basket-like extractor 120 which includes a plurality of arms 122, one end of each of which being affixed to a solid or tubular mandrel 124, the other end of each of which being attached to or looped about a hollow basket 126. The basket 126 includes a proximal generally cylindrical portion 127 and a distal portion 128 integrally extended therefrom in a cone-like matter. The very distal end portion of the distal portion 128 surrounds the mandrel 124 such that it can slide independently over the mandrel 124.

Figure 12:
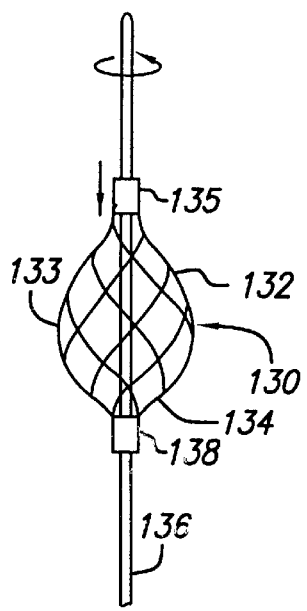
FIG. 12 is a schematic illustration depicting a ninth embodiment of the extraction device of the present invention.

A ninth embodiment in the present invention is depicted in FIG. 12. In this embodiment, the extractor includes a hollow knitted or mesh structure 132 that has a generally cylindrical mid-section 133, and proximal 134 and distal 135 portions integrally extending from the mid-section 133 and which narrow in a cone-like manner therefrom. The proximal portion 134 is welded or otherwise affixed to a solid or tubular mandrel 136. The distal portion 135 surrounds the mandrel 136 in a manner such that the distal portion can slide independently of the mandrel 136. A collar 138 can be employed to aid in affixing the proximal end 134 to the mandrel 136.

Figure 13:
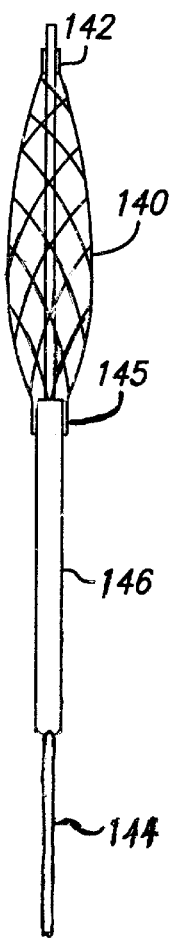
FIG. 13 is a schematic illustration depicting a tenth embodiment of the extraction device of the present invention.

As shown in FIG. 13, a tenth embodiment of the present invention includes a braided or knitted balloon 140. A distal end 142 of the balloon 140 is attached to a distal end of a central mandrel 144, whereas its proximal end is attached to a distal end 145 of an elongate outer tube assembly 146. In the presently preferred embodiment, the mandrel 144 is configured longitudinally within the outer tube assembly 146. It is also contemplated that the mandrel 144 have a length greater than the outer tube 146 so that an operator can grasp both the mandrel 144 and outer tube assembly 146 independently. Through manipulation of the outer tube assembly 146 independently of the mandrel 144, the braided balloon 140 can be caused to expand or contract radially.

In order to manufacture the knitted or braided structure of the aforementioned extractors, either a plurality of wires or a single wire can be used. It is contemplated that the wires be comprised of Nitinol or other materials having similar properties. In the event a plurality of wires are used to form the knitted or mesh structures, four spaced-apart wires for example, may be wrapped in helical fashion in a clockwise direction about a mandrel (not shown) having a desired profile. The forming mandrel itself is used to define the profile of the resulting extractor configuration. An additional like number of spaced wires could simultaneously be helically wrapped in a counter clockwise direction in an over/under pattern with the wires being wrapped about the mandrel in a clockwise direction to thereby form the desired knitted or mesh configuration. Alternatively, a single wire can be wrapped in a helical fashion about a mandrel (not shown) that includes a plurality of pegs extending from the ends of the mandrel, the pegs being employed to aid in reversing the direction of winding. An over/under pattern of winding may also be employed to produce the desired knitted or mesh structures. A particular advantage of using one wire to form the knitted or mesh structure is that such a resultant structure is characterized by having atraumatic ends, a high expansion ratio and high flexibility.

The size of the filament or wire employed to construct the braid as well as angles between the filaments can be selected for the particular application. Moreover, the radial and longitudinal dimensions of the braid structure can likewise be varied for a particular application. However, the same effective range of dimensions contemplated for the second and third embodiments described above would be acceptable for the knitted or braided embodiments.

Figure 14:
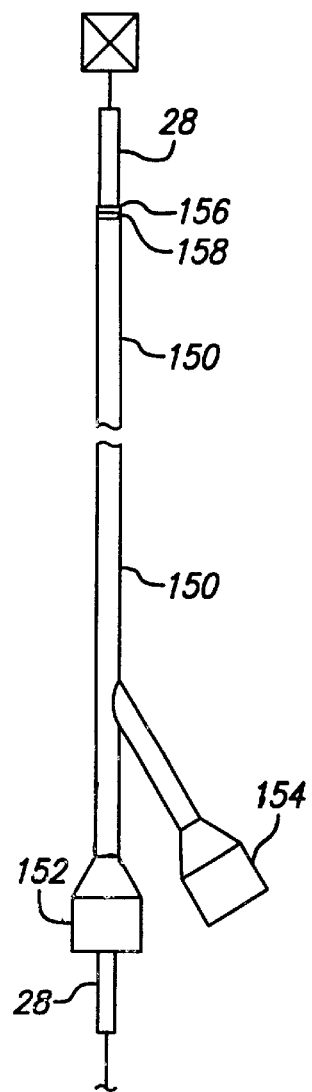
FIG. 14 is a plan view of the present invention being deployed within an insertion catheter with a side suction port.

The extractors/filters and delivery catheter systems heretofore described are also contemplated to be used with an insertion catheter. A particularly useful insertion catheter is illustrated in FIG. 14 (the extractor being schematically represented at a distal end of the assembly). The insertion catheter 150 is hollow with a single lumen and has a Y junction towards its proximal end. The insertion catheter is a standard commercially available catheter. The insertion catheter has two ports, 152 and 154. Port 152 is in straight communication with the longitudinal axis of the insertion catheter 150 and is useful for the insertion of the delivery catheter 28 and an extractor of the present invention and mandrels associated therewith. The other port, which is angled away from the longitudinal axis of the insertion catheter, is for the attachment to a suction line from a vacuum source. Located at the distal end 156 of the insertion catheter is a marker band 158 that can be located via radiographic means while the insertion catheter is being used.

In practice, the insertion catheter 150 is inserted through a large vessel and through the vascular system to a position near a clot or foreign body in an occluded artery under fluoroscopic guidance. The delivery catheter 28 is then inserted through port 152 and through the insertion catheter 150 such that the distal end of the catheter 28 has passed the distal end 156 of the insertion catheter 150. The delivery catheter 28 or extractor is then translated across the clot or foreign body (not shown). The mandrel is then translated proximally to ensnare the foreign body or clot which is then translated toward the distal end 156 of the insertion catheter 150. Once the clot or foreign body is at the distal end 156, suction is applied via port 154 to suck part of the same into the distal end 156. Thereafter, the insertion catheter 150, the delivery catheter 28, the extractor and undesirable material are removed from the patient.

It is also contemplated that the present invention can be used as a filter in a blood vessel. In such a situation, the above-described extractors are deployed within a blood vessel and held stationary for a period of time sufficient for the extractor to remove unwanted material from a patient's bloodstream.

Thus, an extractor system is disclosed which allows for the removal of thromboembolic material and foreign bodies from a blood vessel. While several particular forms and applications of the invention have been illustrated and described, it will be apparent to those skilled in the art that many more modifications are possible without departing from the spirit and scope of the invention. The invention, therefore, is not to be restricted except in the spirit of claims appended hereto.

I claim:

1. A device for removing unwanted material from vasculature, comprising:

an elongate wire having a distal end; and at least two radially extending structures spaced apart longitudinally along the elongate wire proximate the distal end, at least one radially extending structure including a loop having a rounded atraumatic end, the loop originating and terminating at a substantially common longitudinal position on the elongate wire.

2. The device of claim 1, wherein the radially extending structures have a different outside radius.

3. The device of claim 2, wherein a distal most radially extending structure has a larger outside radius than the adjacent radially extending structure.

4. The device of claim 1, wherein each radially extending structure is affixed to the elongate wire such that rotation of the wire entangles the radially extending structures in the unwanted material.

5. The device of claim 1, wherein each radially extending structure comprises a plurality of loops arranged in an annular radial array about the circumference of the wire.

6. The device of claim 1, wherein certain of the radially extending structures overlay an adjacent radially extending structure.

7. The device of claim 1, wherein the radially extending structures extend transversely to the elongate wire.

8. The device of claim 1, wherein the elongate wire has a length sufficient to extend from within a patient's vasculature to outside the patient's vasculature.

9. The device of claim 1, wherein the device is configured to be used with a delivery catheter.

10. The device of claim 9, wherein the delivery catheter is configured to retain the device in a radially compressed configuration.

* * * * *